United States Patent
Kim et al.

(10) Patent No.: US 9,912,790 B2
(45) Date of Patent: Mar. 6, 2018

(54) STERILIZING APPARATUS FOR PORTABLE TERMINAL

(71) Applicant: Seoul Viosys Co., Ltd., Ansan-si (KR)

(72) Inventors: Jong Rack Kim, Ansan-si (KR); Daewoong Suh, Ansan-si (KR); Jung Youl Park, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 0 days.

(21) Appl. No.: 14/775,511

(22) PCT Filed: Mar. 10, 2014

(86) PCT No.: PCT/KR2014/001963
§ 371 (c)(1),
(2) Date: Sep. 11, 2015

(87) PCT Pub. No.: WO2014/142493
PCT Pub. Date: Sep. 18, 2014

(65) Prior Publication Data
US 2016/0036952 A1    Feb. 4, 2016

(30) Foreign Application Priority Data

Mar. 14, 2013  (KR) .......................... 10-2013-0027390

(51) Int. Cl.
*H04M 1/17* (2006.01)
*A61L 2/10* (2006.01)
(Continued)

(52) U.S. Cl.
CPC ................. *H04M 1/17* (2013.01); *A61L 2/10* (2013.01); *H04B 1/3888* (2013.01); *H04M 1/04* (2013.01);
(Continued)

(58) Field of Classification Search
CPC ........ H04M 1/17; H04M 1/04; H04B 1/3888; A61L 2/10; A61L 2/24; A61L 2/00; A61L 2/26; G21K 5/08; H04W 4/008; H05K 5/00
(Continued)

(56) References Cited

U.S. PATENT DOCUMENTS

2006/0188389 A1    8/2006  Levy
2008/0265179 A1*  10/2008  Havens .................... A61L 2/10
                                                               250/492.1
(Continued)

FOREIGN PATENT DOCUMENTS

KR    10-2011-0083073 A1    7/2011
KR    10-2012-0041518 A1    5/2012
(Continued)

OTHER PUBLICATIONS

Yang, Jeong Rok, Authorized Officer, International Search Report, International Patent Application No. PCT/KR2014/001963, dated Jul. 17, 2014, 2 pages.

*Primary Examiner* — Khawar Iqbal
(74) *Attorney, Agent, or Firm* — Perkins Coie LLP

(57) ABSTRACT

Disclosed herein is a sterilization apparatus for a portable terminal, including a casing configured to receive the portable terminal and a UV LED provided in the casing. The sterilization apparatus can be always carried along with a portable terminal because the sterilization apparatus is constructed using a casing or a cover attached to the portable terminal. Accordingly, the portable terminal can be easily sterilized while in motion without being limited to the place.

16 Claims, 3 Drawing Sheets

(51) Int. Cl.
*H05K 7/02* (2006.01)
*H04B 1/3888* (2015.01)
*H04M 1/04* (2006.01)
*H04W 4/00* (2018.01)
*A45C 15/00* (2006.01)
*A45C 11/00* (2006.01)

(52) U.S. Cl.
CPC ............. *H04W 4/008* (2013.01); *A45C 15/00* (2013.01); *A45C 2011/002* (2013.01); *A61L 2202/16* (2013.01); *A61L 2202/18* (2013.01)

(58) Field of Classification Search
USPC .......... 455/575.1–575.8; 250/455.11, 354.1, 250/372, 504 R
See application file for complete search history.

(56) References Cited

U.S. PATENT DOCUMENTS

| | | | | |
|---|---|---|---|---|
| 2009/0323306 | A1* | 12/2009 | Son | F21V 9/16 362/84 |
| 2013/0063922 | A1* | 3/2013 | La Porte | A61L 2/10 361/807 |
| 2014/0183377 | A1* | 7/2014 | Bettles | A61L 2/10 250/455.11 |
| 2014/0264075 | A1* | 9/2014 | LaPorte | A61L 2/00 250/455.11 |
| 2014/0355306 | A1* | 12/2014 | Seo, II | G02B 6/0068 362/612 |
| 2015/0064064 | A1* | 3/2015 | Kim | A61L 2/10 422/24 |
| 2015/0158741 | A1* | 6/2015 | Lee | C02F 1/003 210/184 |
| 2015/0250913 | A1* | 9/2015 | Matsui | F24F 3/16 250/436 |
| 2016/0074545 | A1* | 3/2016 | Kim | A61L 2/10 250/455.11 |
| 2017/0040307 | A1* | 2/2017 | Lee | H01L 25/167 |

FOREIGN PATENT DOCUMENTS

| | | | |
|---|---|---|---|
| KR | 10-2012-0066909 A1 | 6/2012 | |
| KR | 10-1191356 B1 | 10/2012 | |
| KR | 101191356 B1 * | 10/2012 | ............. A45C 11/00 |

* cited by examiner

[Fig. 1]
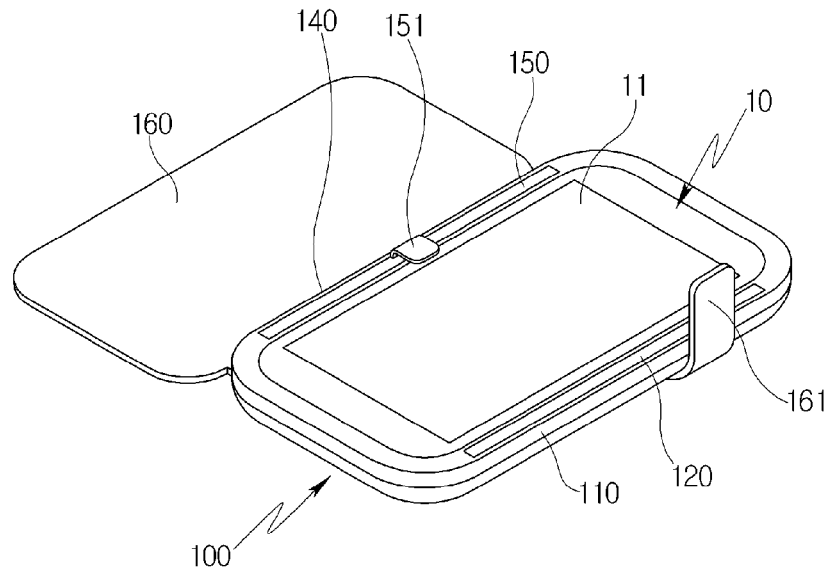
[Fig. 2]
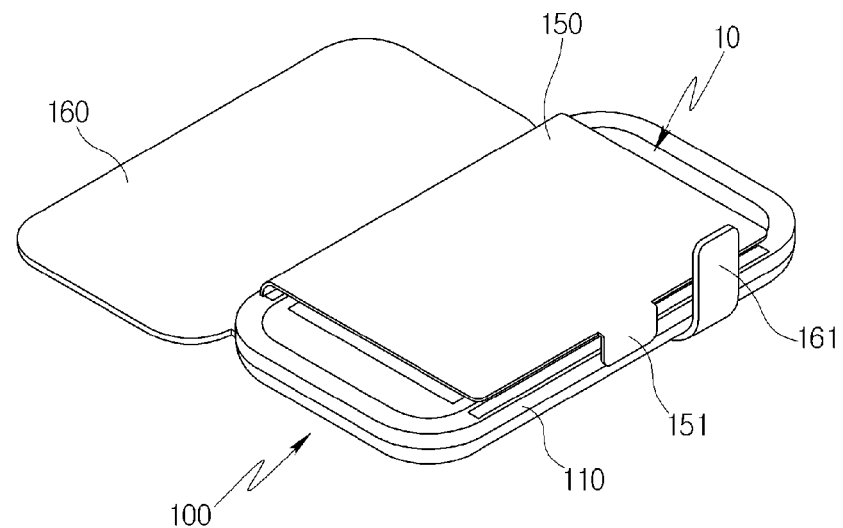
[Fig. 3]
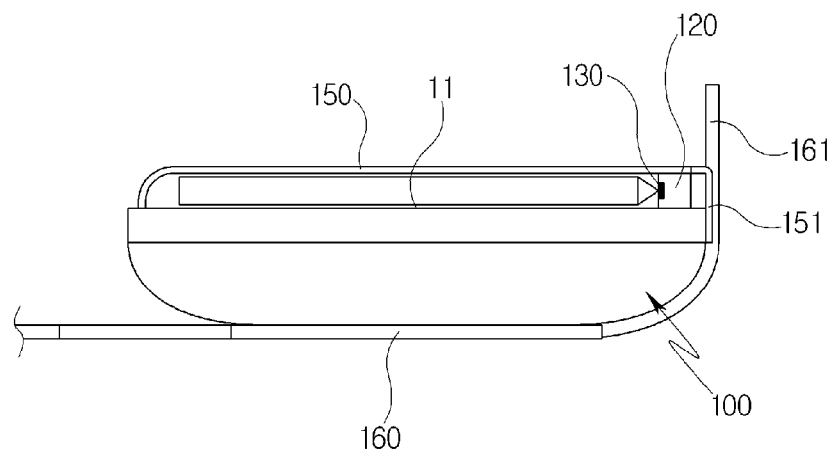

[Fig. 4]
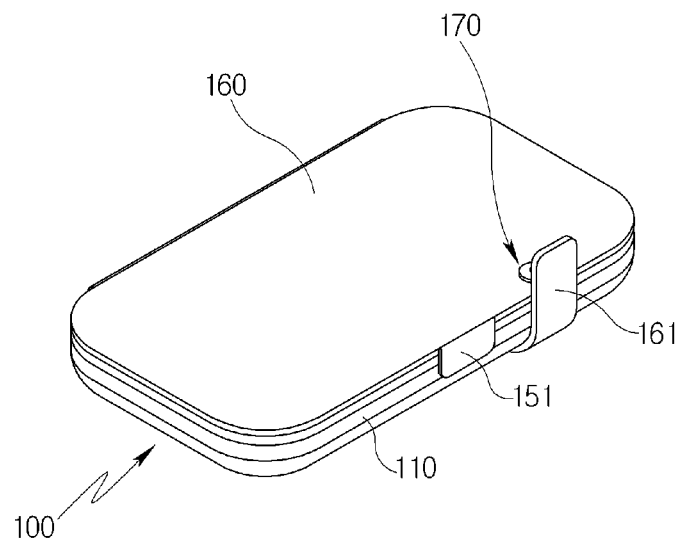
[Fig. 5]
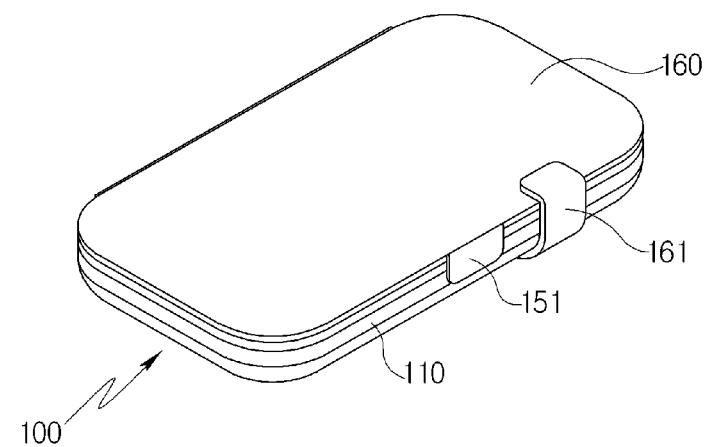
[Fig. 6]
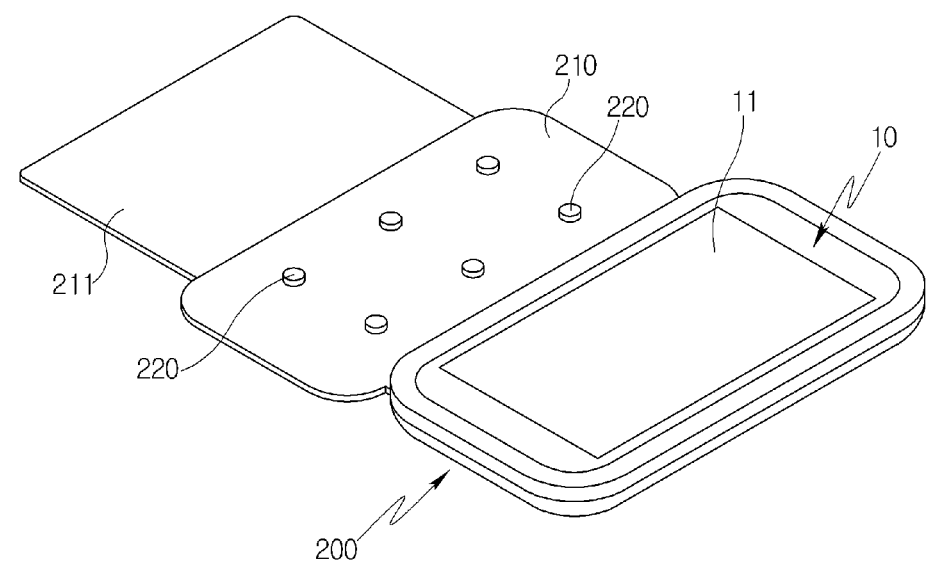

[Fig. 7]
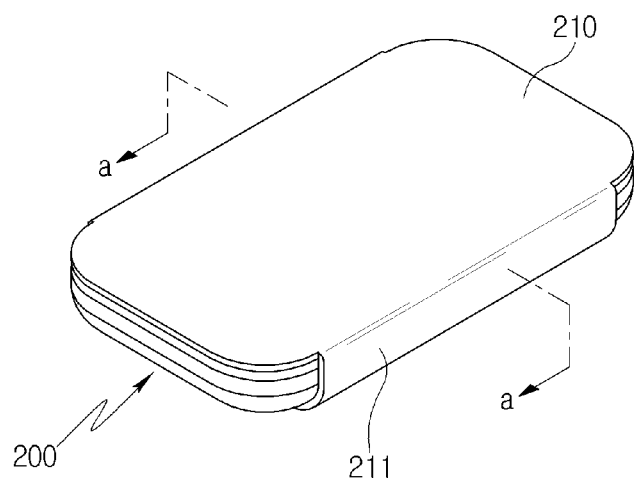
[Fig. 8]
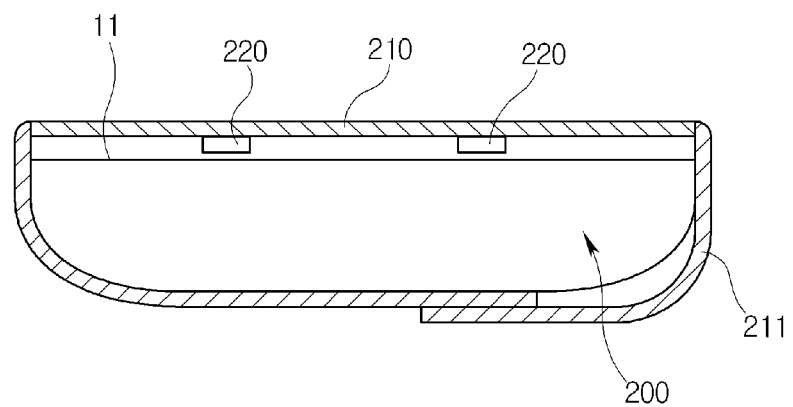

STERILIZING APPARATUS FOR PORTABLE TERMINAL

CROSS REFERENCE TO RELATED APPLICATION

This patent document is a 35 U.S.C. § 371 National Stage application of PCT Application No. PCT/KR2014/001963, filed on Mar. 10, 2014, which further claims the benefits and priority of prior Korean Patent Application No. 10-2013-0027390, filed on Mar. 14, 2013. The entire disclosures of the above applications are incorporated by reference in their entirety as part of this document.

TECHNICAL FIELD

Exemplary embodiments of the present invention relates to a sterilization apparatus for a portable terminal, and more particularly, to a sterilization apparatus for a portable terminal, which is capable of sterilizing a portable terminal using an UltraViolet Light Emitting Diode (UV LED) for radiating UV.

BACKGROUND ART

A portable terminal, for example, a mobile phone has been generalized to the extent that almost all people including teenagers as well as adults carry the mobile phone and has been settled as one of necessities in modern life.

Such a portable terminal provides very great convenience in the life of the modern humans, but also gives a harmful influence on a user's body due to various viruses that are present in the portable terminal because the portable terminal is always carried.

In particular, a recent portable terminal includes a touch screen that operates in response to a touch operation using a hand. In this case, if a screen region of the portable terminal is unsanitary, a user is exposed to a danger of being infected with a harmful virus.

A sterilization apparatus for sterilizing a portable terminal has been proposed. For example, Korean Patent Application Publication No. 10-2013-0005941 entitled "A Sterilizer of a Portable Telephone" was proposed.

A conventional sterilization apparatus for a portable terminal including the disclosed patent, however, has low portability because it needs to be additionally provided apart from a portable terminal. Furthermore, the conventional sterilization apparatus has a problem in that it cannot sterilize a portable terminal in motion with the portable terminal carried on because the conventional sterilization apparatus is used with it carried on the portable terminal in an office or at home.

DISCLOSURE OF INVENTION

Technical Problem

An embodiment of the present invention relates to a sterilization apparatus for a portable terminal, which is capable of being always carried along with a portable terminal and easily sterilizing the portable terminal while in motion without being limited to the place by constructing the sterilization apparatus using a casing or a cover attached to the portable terminal.

Solution to Problem

A sterilization apparatus for a portable terminal in accordance with a first embodiment of the present invention may include a casing configured to receive the portable terminal and a UV LED provided in the casing. The sterilization apparatus may further include a reflection part configured to reflect UV radiated from the UV LED. Alternatively, the sterilization apparatus may further include a cover connected to the casing and configured to cover the portable terminal.

In the sterilization apparatus for a portable terminal in accordance with the first embodiment of the present invention, the UV LED may radiate UV to one surface of the portable terminal.

In the sterilization apparatus for a portable terminal in accordance with the first embodiment of the present invention, the casing may include a first side part covering one side of the portable terminal, a protrusion part may be provided on the top of the first side part, and the UV LED may be provided in the protrusion part.

In the sterilization apparatus for a portable terminal in accordance with the first embodiment of the present invention, the UV LED is provided on the side of the protrusion part directed toward one surface of the portable terminal and may be configured to radiate UV to the one surface of the portable terminal.

In the sterilization apparatus for a portable terminal in accordance with the first embodiment of the present invention, the protrusion part may be provided in such a way as to appear and disappear within the first side part in response to a pressing operation.

In the sterilization apparatus for a portable terminal in accordance with the first embodiment of the present invention, the casing may include a second side part covering the other side of the portable terminal. The sterilization apparatus further may include a reflection part capable of switching between a first state in which the reflection part is wound in a roll form and received within the second side part and a second state in which the reflection part unwinds from the first state through the top of the second side part and covers one surface of the portable terminal.

In the sterilization apparatus for a portable terminal in accordance with the first embodiment of the present invention, a hook part may be formed at the end of the reflection part, and the reflection part can maintain the second state when the hook part is supported by the side of the first side part.

In the sterilization apparatus for a portable terminal in accordance with the first embodiment of the present invention, the UV LED may radiate UV after the reflection part switches from the first state to the second state.

In the sterilization apparatus for a portable terminal in accordance with the first embodiment of the present invention, the sterilization apparatus may further include a cover connected to the casing and configured to cover the one surface of the portable terminal or the top of the reflection part in the second state. The UV LED may radiate UV after the reflection part switches to the second state and the cover covers the top of the reflection part.

A sterilization apparatus for a portable terminal in accordance with a second embodiment of the present invention may include a cover configured to have one side connected to the portable terminal or to a casing for receiving the portable terminal and to cover one surface of the portable terminal and a UV LED provided on one surface of the cover facing the one surface of the portable terminal and configured to radiate UV to the one surface of the portable terminal.

In the sterilization apparatus for a portable terminal in accordance with the first and the second embodiments of the present invention, the sterilization apparatus may further include a power source unit configured to supply a power source to the UV LED.

In the sterilization apparatus for a portable terminal in accordance with the first and the second embodiments of the present invention, the power source unit may include a Near Field Communication (NFC) antenna provided in the portable terminal and a magnetic induction antenna configured to convert electromagnetic waves received from the NFC antenna into an electrical signal and supply a power source to the UV LED.

In the sterilization apparatus for a portable terminal in accordance with the first and the second embodiments of the present invention, the supply of the power source to the UV LED using the power source unit may be controlled by an application installed in the portable terminal.

Advantageous Effects of Invention

In accordance with the present invention, there is an advantage in that the portability of the sterilization apparatus for a portable terminal is greatly improved because the UV LED is included in the casing or the cover attached to the portable terminal.

Furthermore, there is an advantage in that use convenience is greatly improved because a screen region of a portable terminal can be easily sterilized using UV generated from the UV LED provided in the casing or the cover of the portable terminal.

Furthermore, a structurally simplified sterilization apparatus not including additional power supply means can be provided because the power source unit using Near Field Communication (NFC) technology is included in the sterilization apparatus.

BRIEF DESCRIPTION OF DRAWINGS

FIG. 1 is a perspective view showing a sterilization apparatus for a portable terminal in accordance with a first embodiment of the present invention.

FIG. 2 is a perspective view showing a state in which a reflection part of FIG. 1 switches to a second state.

FIG. 3 is a side view of the sterilization apparatus for a portable terminal shown in FIG. 2.

FIGS. 4 and 5 show states in which a cover and a fixing piece shown in FIG. 1 are combined and used.

FIG. 6 is a perspective view showing a sterilization apparatus for a portable terminal in accordance with a second embodiment of the present invention.

FIG. 7 is a perspective view showing a state in which a cover shown in FIG. 6 has been rotated.

FIG. 8 is a side view of the sterilization apparatus for a portable terminal shown in FIG. 7.

MODE FOR THE INVENTION

Hereinafter, a sterilization apparatus for a portable terminal in accordance with a first embodiment of the present invention is described with reference to accompanying drawings.

FIG. 1 is a perspective view showing an sterilization apparatus for a portable terminal in accordance with a first embodiment of the present invention, FIG. 2 is a perspective view showing a state in which a reflection part of FIG. 1 switches to a second state, FIG. 3 is a side view of the sterilization apparatus for a portable terminal shown in FIG. 2, and FIGS. 4 and 5 show states in which a cover and a fixing piece shown in FIG. 1 are combined and used.

As shown in FIGS. 1 to 3, sterilization apparatus for a portable terminal in accordance with the first embodiment of the present invention may include a casing 100 configured to have a portable terminal 10 received therein and an UV LED 130 provided in the casing 100.

The portable terminal 10 may be, for example, a mobile phone. A screen region 11 for enabling a user to visually check an operation state of the portable terminal 10 is formed on a top surface of the portable terminal 10. Furthermore, the screen region 11 may be a touch screen.

The portable terminal 10 can be received in the casing 100. Here, the portable terminal 10 may be received in the casing 100 in the state in which the screen region 11 of the portable terminal 10 is exposed. The casing 100 is configured to protect at least one of the sides of the portable terminal 10 in the state in which the portable terminal 10 is received in the casing 100. In the illustrated example, the casing 100 is configured to cover the four sides and bottom of the portable terminal 10.

In the illustrated example, the casing 100 includes a first side part 110 for covering and protecting one surface of the portable terminal 10. Here, a protrusion part 120 equipped with the UV LED 130 may be formed in the first side part 110.

As shown in FIG. 3, the protrusion part 120 may be upwardly protruded from the top of the first side part 110. In such a protrusion state, any one (i.e., the left side in the example of FIG. 3) of the sides of the protrusion part 120 is directed toward the screen region 11 of the portable terminal 10.

The UV LED 130 may be provided on the left side of the protrusion part 120. Here, one UV LED 130 may be provided, or a plurality of the UV LEDs 130 spaced apart from one another in the length direction of the protrusion part 120 may be provided.

The UV LED 130 provided in the protrusion part 120 radiates UV in the direction of the screen region 11. One side of the portable terminal 10 including the screen region 11 can be sterilized by the UV radiated from the UV LED 130.

The protrusion part 120 may be provided so that it is always protruded from the first side part 110, but may be configured to be protruded if necessary. To be concrete, the protrusion part 120 may be provided in such a way as to be protruded or retracted up and down within the first side part 110. Although the protrusion part 120 has not been illustrated as being protruded or retracted, the protrusion part 120 may have a variety of known push-button switch structures, that is, a structure in which a button unit is pressed and inserted when a pressing operation is performed and the button unit is protruded when a pressing operation is performed again. If such a structure is included, the protrusion part 120 can be upwardly protruded from the top of the first side part 110 in response to a user's pressing operation as shown in FIG. 3. If a pressing operation is performed again, the protrusion part 120 can be inserted into the first side part 110 without being protruded from the top of the first side part 110, as shown in FIG. 1. Accordingly, when a user performs a pressing operation if it is necessary to sterilize the portable terminal 10, the protrusion part 120 is protruded and at the same time the UV LED 130 is externally exposed, with the result that a sterilization operation can be performed. Furthermore, when a user performs a pressing operation on the protrusion part 120 again if a sterilization operation is not necessary, the protrusion part 120 can be inserted into the first side part 110.

The casing 100 may include a second side part 140 for covering and protecting the other side of the portable terminal 10. The other side of the portable terminal 10 that is covered with the second side part 140 may be a side opposite one surface of the portable terminal 10. That is, the first side part 110 and the second side part 140 may be opposite each other.

The second side part 140 may be equipped with a reflection part 150. The reflection part 150 has a reflection layer for reflecting UV to one surface of the reflection part 150 that faces the screen region 11 so that the UV radiated from the UV LED 130 can reach a portion far from the UV LED 130 on the screen region 11. The reflection part 150 is made of materials that reflect UV. Accordingly, one surface itself of the reflection part 150 may be the reflection layer, or the reflection layer may be formed by coating a reflection substance on one surface of the reflection part 150 that faces the screen region 11.

In the state in which the reflection part 150 is disposed to cover the screen region 11 as shown in FIG. 2, a passage for UV is provided between the space between the bottom of the reflection part 150 and the top of the screen region 11 as shown in FIG. 3. Accordingly, the UV can reach a place far from the UV LED 130 on the screen region 11.

The reflection part 150 needs to be disposed to cover the screen region 11 as shown in FIG. 2 only when the screen region 11 needs to be sterilized, and the reflection part 150 should not cover the screen region 11 as shown in FIG. 1 if the screen region 11 is not sterilized. To this end, the reflection part 150 may be provided in such a way to be wound or unwound if necessary. More particularly, the reflection part 150 may be provided in such a way to switch between a first state (refer to FIG. 1) in which the reflection part 150 is wound in a roll form and received in the second side part 140 and a second state (refer to FIG. 2) in which the reflection part 150 is unwound along the top of the second side part 140 and disposed to cover one surface of the portable terminal 10. A rotation shaft (not shown) for winding or stretching the reflection part 150 so that the reflection part 150 can be wound or unwound as described above may be provided in the second side part 140. Furthermore, various rotation means for rotating the rotation shaft clockwise or counterclockwise, for example, rotation means (not shown) combined with the rotation shaft, such as a torsion spring, so that the reflection part 150 switches from the second state to the first state may be provided in the second side part 140. A detailed structure for enabling the reflection part 150 to be unwound in the state in which the reflection part 150 has been wound in a roll form may be easily known from a known blind structure of a roll form, and thus a further description thereof is omitted.

If the reflection part 150 is pulled by a user and unwound and thus the reflection part 150 switches to the second state, the reflection part 150 needs to maintain the second state until a sterilization operation using the UV LED 130 is completed. To this end, a hook part 151 may be provided at the end of the reflection part 150. In the illustrated example, the hook part 151 has been illustrated as having a cross section of a ']' shape. When the reflection part 150 switches to the second state, the hook part 151 is engaged with the side of the first side part 110 and can be supported by the side of the first side part 110. When the hook part 151 is supported as described above, the reflection part 150 can maintain the second state. If a sterilization operation is completed and thus the reflection part 150 needs to be wound again, the hook part 151 can be detached from the side of the first side part 110 by lifting up the hook part 151. In this case, the rotation shaft is rotated reversely by the rotation means, so the reflection part 150 can be wound again.

A user's body does not need to be exposed to UV radiated from the UV LED 130 because the UV radiated from the UV LED 130 is harmful to the human body. Accordingly, a sterilization operation using the UV LED 130 may be performed in the state in which the reflection part 150 has switched to the second state, that is, in the state in which UV radiated from the UV LED 130 is blocked by the reflection part 150 without being exposed externally if possible. To this end, the sterilization operation of the UV LED 130 may be performed after the reflection part 150 switches to the second state. More particularly, a control unit for controlling the supply of power to the UV LED 130 is provided. The control unit can control power so that the power is supplied to the UV LED 130 when a state in which the reflection part 150 has switched to the second state is checked by a sensor, for example.

Alternatively, in constructing an electrical circuit between the UV LED 130 and a power source unit to be described later, contact points may be formed on the side of the first side part 110 and the hook part 151 that is latched and supported by the side of the first side part 110. When the hook part 151 is latched and supported by the first side part 110, that is, when the contact points are electrically connected, an electric current to the electrical circuit may be turned on.

The present embodiment may further include a cover 160 connected to the casing 100. The cover 160 has one side connected to the casing 100. The cover 160 can be rotatably moved around the one side connected to the casing 100. When the cover 160 rotatably moves and thus the reflection part 150 switches to the first state, the cover 160 covers the screen region 11. When the reflection part 150 switches to the second state, the cover 160 covers the top of the reflection part 150. Here, the sterilization operation of the UV LED 130 may be performed after the reflection part 150 has switched to the second state and the cover 160 has rotatably moved in such a way as to cover the top of the reflection part 150.

To this end, the present embodiment may further include a fixing piece 161 connected to the casing 100 and coupling means 170 (refer to FIG. 4). The coupling means 170 functions to combine one surface of the fixing piece 161 with a corresponding surface of the cover 160 detachably such that the cover 160 is not rotated reversely in the state in which the cover 160 covers the screen region 11 or the cover 160 has rotatably moved in such a way as to cover the top of the reflection part 150 in the second state. The fixing piece 161 may be disposed on the side of the first side part 110 in the state in which the fixing piece 161 is connected to the casing 100. The fixing piece 161 may have a length that is protruded upwardly from the first side part 110 as shown in FIG. 4. The fixing piece 161 may be made of elastically deformed materials or may be bent. When the cover 160 rotatably moves in such a way as to cover the screen region 11 or the top of the reflection part 150 in the second state, the end of the fixing piece 161 may be detachably combined with one side of the cover 160 as shown in FIG. 5 so that the cover 160 is not rotated reversely. Various means, such as a snap button or a magnet, may be used as the coupling means 170 for combining the fixing piece 161 with the cover 160. The snap buttons or the magnets may be formed on one surface of the fixing piece 161 and a surface of the cover 160 corresponding to the one surface of the fixing piece 161, respectively, and detachably combined. Here, in constructing the electrical circuit between the UV LED 130 and the power source unit to be described later, contact points may be formed in the fixing piece 161 and the coupling means 170 formed in the cover 160. When the fixing piece 161 is combined with the cover 160, that is, when the contact points formed in the fixing piece 161 and the cover 160 are electrically connected, an electric current on the electrical circuit may be turned on.

In accordance with the present embodiment, when the reflection part 150 switches to the second state or the cover 160 has rotatably moved in such a way as to cover the top of the reflection part 150 in the example in which the cover 160 is further included, the UV LED 130 may be driven so that a user's body is prevented from being exposed to UV radiated from the UV LED 130.

The present embodiment includes the power source unit for supplying a power source to the UV LED 130. The power source unit may include additional battery or may supply a power source to the UV LED 130 using the battery of the portable terminal 10. Alternatively, the present embodiment may further include a magnetic induction antenna for converting electromagnetic waves, received from a Near Field Communication (NFC) antenna included in the portable terminal 10, into an electrical signal and supplying a power source to the UV LED 130. Here, NFC is one of Radio Frequency Identifications (RFIDs), and it refers to technology in which data is transmitted between terminals in a close distance of about 10 cm using a contactless near-field wireless communication module using a frequency band of 13.56 MHz. The portable terminal 10 may be equipped with the NFC antenna so that such an NFC function can be performed. The casing 100 may be equipped with the magnetic induction antenna disposed to face the NFC antenna. When the NFC antenna is activated, an induced current is also generated in the magnetic induction antenna. That is, the magnetic induction antenna converts electromagnetic waves, received from the NFC antenna, into an electrical signal. The UV LED 130 emits light by way of the generated induced current, thus radiating UV. In order to control the NFC antenna so that the NFC antenna is activated, a method using an application installed in the portable terminal may be used. The application may be written to perform a function of controlling the driving of the NFC antenna. If such an application is used, the NFC antenna can be controlled by a user's setting so that the NFC antenna operates under a condition that it does not operate, such as that the display of the portable terminal is turned off. As a result, a sterilization operation can be performed on the portable terminal. In the present embodiment, since the power source unit using NFC technology is included as described above, a sterilization operation using the UV LED 130 can be performed even without using additional power supply means.

A sterilization apparatus for a portable terminal in accordance with a second embodiment of the present invention is described in detail below with reference to the accompanying drawings.

FIG. 6 is a perspective view showing a sterilization apparatus for a portable terminal in accordance with a second embodiment of the present invention, FIG. 7 is a perspective view showing a state in which a cover shown in FIG. 6 has been rotated, and FIG. 8 is a side view of the sterilization apparatus for a portable terminal shown in FIG. 7.

As shown, the sterilization apparatus for a portable terminal in accordance with the second embodiment of the present invention includes a cover 210 configured to have one side connected to a portable terminal 10 or to a casing 200 for receiving the portable terminal 10 and to cover one surface of the portable terminal 10 and UV LED 220 provided on one surface of the cover 210 that faces one surface of the portable terminal 10 and configured to radiate UV to one surface of the portable terminal 10.

Like the cover 160 of the first embodiment, the cover 210 has one side connected to the casing 200 and covers the screen region 11 of the portable terminal 10 while rotatably moving. If the casing 200 is not additionally included in the portable terminal 10, the cover 210 may have one side directly connected to the portable terminal 10. An extension part 211 may be further formed at the end of the cover 210. The extension part 211 may surround a side and bottom of the casing 200 in the state in which the cover 210 rotatably moves and covers the screen region 11. In this state, the end of the extension part 211 is detachably fixed to the bottom of the casing 200 or to a portion on one side of the cover 210 that is connected to the bottom of the casing 200 in the state in which the end of the extension part 211 overlaps with the portion on one side of the cover 210. Accordingly, the state in which the cover 210 covers the portable terminal 10 can be maintained.

The UV LED 220 is provided on one surface of the cover 210 that faces the screen region 11. Only one UV LED 220 may be provided, or a plurality of the UV LEDs 220 spaced apart from one another on one surface of the cover 210 may be provided.

Like in the previous embodiment, the present embodiment may include a power source unit for supplying a power source to the UV LED 220. The power source unit may have the same construction as the power source unit described in connection with the first embodiment, and thus a detailed description of the power source unit is omitted.

In the present embodiment, the UV LED 220 is provided on one surface of the cover 210 and configured to face the screen region 11 when the cover 210 rotatably moves. Furthermore, the UV LED 220 is supplied with a power source from the power source unit and configured to radiate UV to the screen region 11. The present embodiment has an advantage in that it does not need to include an additional reflection part as compared with the first embodiment because the UV LED 220 is provided on one surface of the cover 210 that faces the screen region 11 as described above.

Although some detailed embodiments of the present invention have been described above, the embodiments have been provided to describe the present invention in detail, and the present invention is limited to the embodiments. It is evident to those skilled in the art that the present invention may be modified or improved within the technical spirit of the present invention.

Such a simple modification or change of the present invention falls within the scope of the present invention, and a detailed scope of the present invention will become evident by the appended claims.

The invention claimed is:

1. A sterilization apparatus for a portable terminal, comprising:
 a casing configured to receive the portable terminal; and
 an UltraViolet Light Emitting Diode (UV LED) provided in the casing to sterilize the portable terminal;
 a retractable protrusion part located on a first side of the casing and having the UV LED on one side of the retractable protrusion part the retractable protrusion part configured as protruded from the first side in a first state and inserted into the first side in a second state and the UV LED emitting light from the one side of the retractable protrusion part toward the portable terminal along a direction parallel to the portable terminal, and wherein the casing comprises a second side covering a side of the portable terminal, and the sterilization apparatus further comprises a reflection part configure to switching between a third state in which the reflection part is in a roll form and received within the second side and a fourth state in which the reflection part covers one surface of the portable terminal.

2. The sterilization apparatus of claim 1, further comprising a reflection part coupled to the casing and configured to reflect UV light radiated from the UV LED.

3. The sterilization apparatus of claim 1, further comprising a cover connected to the casing and configured to cover the portable terminal.

4. The sterilization apparatus of claim 1, wherein the UV LED is configured to radiate UV light to one surface of the portable terminal.

5. The sterilization apparatus of claim 1, wherein-the UV LED is configured to radiate UV light to the one surface of the portable terminal.

6. The sterilization apparatus of claim 1, comprising: a hook part formed at an end of the reflection part, wherein the hook part is configured to maintain the reflection part in the fourth state when the hook part is supported by a side of the first side part.

7. The sterilization apparatus of claim 1, wherein the UV LED radiates UV light toward the portable terminal when the reflection part is in the fourth state.

8. The sterilization apparatus of claim 1, further comprising a cover connected to the casing and configured to cover the one surface of the portable terminal when the reflection part is in the third state or a top of the reflection part when the reflection part is in the fourth state, wherein the UV LED radiates UV light when the cover covers the top of the reflection part.

9. The sterilization apparatus of claim 1, further comprising a power source unit configured to supply power to the UV LED.

10. The sterilization apparatus of claim 9, wherein the power source unit comprises:

a Near Field Communication (NFC) antenna provided in the portable terminal; and a magnetic induction antenna configured to convert electromagnetic waves received from the NFC antenna into an electrical signal and supply the power to the UV LED.

11. The sterilization apparatus of claim 10, wherein the power source unit is configured to supply the power to the UV LED responsive to an application installed in the portable terminal.

12. The sterilization apparatus of claim 1, comprising a reflection part coupled to the casing.

13. A sterilization apparatus for a portable terminal, comprising:

a casing having a top surface, a bottom surface, and a first side between the top surface and the bottom surface, the casing structured to receive the portable terminal on the top surface of the casing;

a cover connectable to the portable terminal or to the casing and configured to cover a top surface of the portable terminal;

an extension part formed at one end of the cover and covering the first side of the casing, the extension part detachably fixed to the bottom of the casing when the cover is rotatably moved to cover the top surface and operable to maintain the covering of the top surface; and an UltraViolet Light Emitting Diode (UV LED) provided on the top surface of the casing and configured to radiate UV light to the portable terminal to sterilize the portable terminal, the UV LED is retracted such that the UV LED is inserted into the casing and protruded such that the UV LED is located on the first side of the casing, and wherein the casing comprises a second side covering a side of the portable terminal, and the sterilization apparatus further comprises a reflection part configure to switching between a third state in which the reflection part is in a roll form and received within the second side and a fourth state in which the reflection part covers one surface of the portable terminal.

14. The sterilization apparatus of claim 13, further comprising a power source unit configured to supply power to the UV LED.

15. The sterilization apparatus of claim 14, wherein the power source unit comprises:

a Near Field Communication (NFC) antenna provided in the portable terminal; and a magnetic induction antenna configured to convert electromagnetic waves received from the NFC antenna into an electrical signal and supply the power to the UV LED.

16. The sterilization apparatus of claim 15, wherein the power source unit is configured to supply the power to the UV LED when controlled by an application installed in the portable terminal.

* * * * *